United States Patent [19]

Rozario et al.

[11] Patent Number: 4,478,219
[45] Date of Patent: Oct. 23, 1984

[54] TEMPORARY MICROVASCULAR OCCLUDER

[76] Inventors: Rodney A. Rozario, 863 Essex St., Bangor, Me. 04401; Manuel Dujovny, 2573 Wickfield Rd., West Bloomfield, Mich. 48033

[21] Appl. No.: 361,386

[22] Filed: Mar. 24, 1982

[51] Int. Cl.³ .......................................... A61B 17/12
[52] U.S. Cl. ..................................... 128/325; 128/346
[58] Field of Search ................ 128/346, 325, 327, 1.3, 128/354; 24/30.5 S, 30.5 L, 251, 260, DIG. 8, DIG. 9, 503, 505, 515, 517, 535–537, 545, 546, 555; 251/9, 10

[56] References Cited

U.S. PATENT DOCUMENTS

| | | | |
|---|---|---|---|
| D. 190,787 | 6/1961 | Schneider | D83/12 |
| 1,352,978 | 9/1920 | Lantieri et al. | 24/260 |
| 2,406,393 | 8/1946 | Neugass | 128/354 |
| 3,326,217 | 6/1967 | Kerr | 128/325 |
| 3,507,270 | 4/1970 | Ferrier | 128/668 |
| 3,665,926 | 5/1972 | Flores | 128/326 |
| 3,877,434 | 4/1975 | Ferguson et al. | 128/327 |
| 3,911,926 | 10/1975 | Peters | 128/325 |
| 4,016,883 | 4/1977 | Wright | 128/325 |
| 4,024,868 | 5/1977 | Williams | 128/346 X |
| 4,063,561 | 12/1977 | McKenna | 128/1.3 X |
| 4,140,125 | 2/1979 | Smith | 128/325 |
| 4,245,638 | 1/1981 | Lebeck et al. | 128/334 C |
| 4,248,224 | 2/1981 | Jones | 128/DIG. 3 X |
| 4,337,774 | 7/1982 | Perlin | 128/325 |
| 4,390,019 | 6/1983 | Ve Veen et al. | 128/346 X |

FOREIGN PATENT DOCUMENTS

| | | | |
|---|---|---|---|
| 2730691 | 1/1978 | Fed. Rep. of Germany | 128/325 |
| 1268034 | 3/1972 | United Kingdom | 128/327 |

OTHER PUBLICATIONS

Martin Motor Trephine Pamphlet 5-1977.

*Primary Examiner*—Michael H. Thaler
*Attorney, Agent, or Firm*—Samuel Meerkreebs

[57] ABSTRACT

A microvascular occluder produced from a suitable plastic, colored and/or transparent; including a pair of juxtapositionable legs secured together in clamping relation on a blood vessel between a base and a cuff slidable over the legs, in which the cuff is retained on the occluder, and in which an indicia scale can be incorporated on one or both of the legs, and in which the cuff can include magnetically-attractive material and be moved magnetically; and in which the occluder is readily sterilized through conventional procedures, and inexpensive to manufacture so that it is readily expendable after usage. An occluder holder comprising a tubular sleeve, longitudinally slotted for holding two occluders in spaced straddling relation on a blood vessel during microvascular anastomais.

4 Claims, 9 Drawing Figures

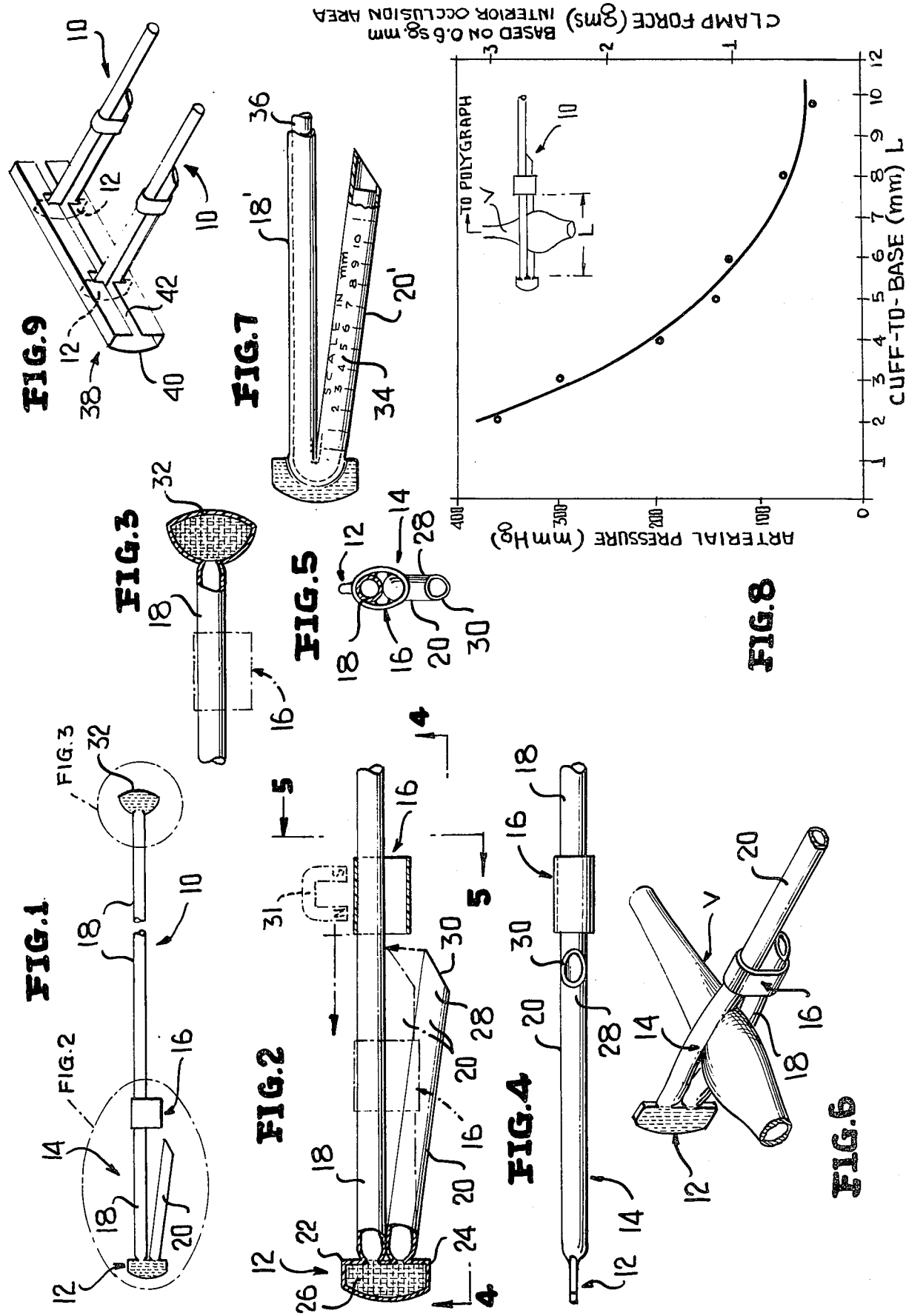

TEMPORARY MICROVASCULAR OCCLUDER

BACKGROUND OF THE INVENTION

1. Field of the Invention

The present invention relates generally to medical and surgical clamps, and more particularly relates to a device for temporarily occluding small vessels during microvascular surgery. Still more particularly, the present invention relates to a relatively minute occluder of the character mentioned in which endothelial damage is substantially minimized; if not eliminated, and thus, thrombosis and anastomosis failure is minimized in a technically adequate procedure.

2. General Background and Prior Art

When a surgeon is engaged in a surgical procedure requiring occlusion of small vessels, it is critical that the device be of a size so as not to impair visual and physical access to the area of the vessel being operated on, and endothelial damage be minimized to avoid thrombosis and anastomosis failure.

A wide variety of miniature aneurysm clips, a microtourniquet and microblock have been proposed in the past; see the "References" below. All of these prior art devices, when observed with a scanning electron microscope, appear to inflict varying degrees of endothelial damage.

In addition to the devices of the "References"; see Appendix I, a vessel ligatures are disclosed in the patents to Flores U.S. Pat. No. 3,665,926, Ferrier, U.S. Pat. No. 3,507,270, Ferguson U.S. Pat. No. 3,887,434 and Jones U.S. Pat. No. 4,248,224.

None of the prior art devices afford the degree of soft pressure control afforded by the invention during microvascular anastomosis.

SUMMARY OF THE INVENTION

The present invention solves many of the problems and shortcomings of the prior art in a simple and inexpensive manner with a device that is easy to construct, simple in operation and use, readily sterilized, and of minimal expense.

More particularly, the occluder of the present invention comprises three components, i.e., a main stem, base and cuff. The main transparent stem comprises a long and short arm terminally connected in hinged, integral relation as the base with the cuff being circumposed and slidable on the long arm and prevented from becoming separated therefrom by a terminal stop. The short arm has a beveled free end facilitating the movement of the cuff thereover to clamp a blood vessel between the arms, and the arms are produced from tubular, polyethelene tubing, or the like, so that cuff pressure is gradually or progressively applied to a clamped blood vessel.

In addition to the general aspects of the invention, features such as magnetically moving the cuff into and out of a clamping position, the use of different materials or colors, as well as different tube (arm) cross sections, and/or reinforcements in the clamp arms are all within the scope of the invention.

BRIEF DESCRIPTION OF THE DRAWING

These together with other objects and the nature of the invention will become apparent from the following detailed description, taken in conjunction with the drawing, forming a part thereof, in which like parts are identified by like reference numerals, wherein:

FIG. 1 is a side elevational view of the occluder of the invention on an enlarged scale;

FIGS. 2 and 3 are enlarged, fragmentary elevations of the portions within the phanton-line ovals identified at FIG. 2 and FIG. 3 on FIG. 1;

FIG. 4 is a bottom plan view of FIG. 2 looking in the direction of line 4—4 of FIG. 2;

FIG. 5 is a sectional view taken on line 5—5 of FIG. 2;

FIG. 6 is a fragmentary perspective view of the occluder in an operative position on a blood vessel;

FIG. 7 is a view similar to FIG. 2, and showing an alternate embodiment;

FIG. 8 is a graphic illustration of a test of the invention plotting arterial pressure (mmHg) or Clamp Force (grams) (based upon 0.6 sq. mm interior occlusion area) in relation to cuff-to-base L (mm); and FIG. 9 is a perspective view of a holding means for orienting a pair of the occluders when straddling a view section.

DESCRIPTION OF PREFERRED EMBODIMENTS

Referring to the drawing in detail, and first considering FIG. 1-5, the microvascular occluder is indicated generally at 10 and comprises three components, a base 12, a stem 14 and cuff 16.

The components are produced from any suitable plastic material such as rubber, silastics, polyethylene, polystyrene, etc., and the working model tested, was produced from a flexible, polyethylene tubing. Construction will be accomplished through conventional molding procedures, all within the skill of the art.

The stem 14 includes a long arm 18 and a short arm 20, each being terminally secured at their adjacent ends 22 and 24, respectively; see FIG. 2, to the base 12 by welding or fusing, or the like, whereby the base and terminal ends of the arms are integrated as indicated at 26. The outer or free end 28 of the short arm 20 is beveled away from the end as indicated at 30 and this facilitates movement of cuff 16 to the phanton-line position in FIG. 2 after the short arm 20 has been pivoted into substantial parallel relation to arm 18, as illustrated in FIGS. 2 and 6, for example.

The cuff 16 comprises a suitably diametered tube section, and will be moved manually into clamping position. Although manual movement is accomplished using forceps or the like, alternatively, the cuff 16 can be impregnated with a magnetically-attractive material, i.e., such as ferrous oxide, or the like, and can be incrementally moved in clamped relation on the arms 18 and 20 by a suitable magnet means 31.

The outer or free end of the long arm 18 is terminally upset or flattened to form a stop or abutment 32 which will prevent inadvertent loss of cuff 16. In regard to loss of the cuff, to facilitate its location and to properly position the same in operative relation on the arms as will be described below, the entire occluder, may be produced in various colors to assist the surgeon and medical assistants in observing and locating the occluder during procedures.

The base 12 acts as the point of flexion between the two arms of the stem and the final shape of the base; note it is flattened as seen in FIG. 4, is produced by the application of heat and pressure to produce the fusing.

The cuff 16 is approximately 2 mm long, i.e., about 1/16 inch long, being produced from a segment of polyethylene tubing with an outer diameter of around 1.7 mm and an inner diameter of about 1.2 mm, which fits snugly, but yet slides over both arms of the stem during application. The arms 18 and 20 are produced from polyethylene tubing having an outer diameter of around 0.6 mm and an inner diameter of about 0.27 mm. The long arm is about 6 cm long, but can be varied in length, and the short arm 20 can be of different lengths, being shown as about 10 mm in FIG. 7, and the scale indicia 34 can be applied to the short (or long) arm 18' as shown in FIG. 7. The dimensions are those of the operative phototype tested and are intended to be illustrative and not restrictive.

Before describing actual tests and operation, it is pointed out that the arms of the disclosed stem provide sufficient clamping and elasticity during release, however, in the event greater resiliency is desired, a steel wire 36, for example can be embedded, in the arm 18' and 20' of the embodiment 10' of FIG. 7.

The selection of tubular arms produced an unusual soft and gradual application of pressure, and cushioning to the vessels being occluded, which was surprisingly unexpected. Although a circular cross sectioned tubing was utilized when producing the prototype, other cross sectioned tubings are within the purview of the invention, i.e., polygonal (triangular, square, rectangular) as well as oval, and even solid cross sections, of compressibility comparable to tubular arms, are contemplated to be within the scope of the invention.

APPLICATION TECHNIQUE

Referring to FIG. 6, after the standard preparation of a vessel, for microvascular anastomosis, the occluder 10 is passed under the vessel V with the short arm 20, uppermost. Arms 18 and 20 are brought together gently and the cuff is placed in position, as shown in FIG. 2. The distance between the base and the cuff can be varied. When blanching of the vessel between the two arms and cessation of transmitted pulsation is seen, occlusion has been effected. Incorrect positioning results in slippage of the occluder with each arterial pulsation.

The advantage of the long arm is that it permits rotation of the vessel into the optimal position during anastomosis. Upon completion of the procedure, the cuff can be withdrawn partially while the vessel is still in the occluder. This permits control of blood flow through the anastomosis, so that the suture line can be observed for signs of potential leakage.

MECHANICAL EVALUATION (FIG. 8)

The following experiment was undertaken to test the mechanical effectiveness of the occluder. An 8 mm segment of carotid artery, measuring 1 mm diameter, was resected from a 450-g Sprague-Dawley rat and was washed free of all blood elements with Ringer's lactate solution. The distal end of a polyethylene tube (PE 190) was placed under an operating microscope, and two shallow annular grooves were cut adjacent to one another. One end of the arterial segment was then placed over the tube for a distance of 3 mm and was secured in place with two 7.0 silk ties, with the precut groove used to anchor the sutures. The proximal end of the tube was connected to a Statham transducer (Statham Instruments Division, Gould, Inc., Oxnard, Calif.) and a Grass polygraph (Grass Instrument Co., Quincy, Mass.). The system was filled with normal saline, free of air bubbles and was zeroed for pressure recording.

For the purpose of the experiment, an occluder with a short arm 14 mm long was constructed to permit recording of applications with a cuff-to-base distance between 2 and 10 mm. With the operating microscope at $25\times$ magnification, the occluder was placed on the distal end of the arterial segment. The first application was at a base-to-cuff distance of 10 mm. The pressure in the system was increased gradually by injecting normal saline into the transducer with a tuberculin syringe. Through the microscope, the point at which either slippage of the occluder or saline leakage was first observed was noted, and the pressure was recorded. Further pressure readings were obtained at cuff-to-base distances of 8, 6, 5, 4, 3, and 2 mm, and a graph was constructed with these measurements.

To obtain an estimate of the "clamp force" exerted by the occluder, we used the following method to evaluate the occluding area during the application. Evans blue dye was injected into the transducer with the occluder applied at a cuff-to-base distance of 4 mm and a pressure of 100 mm Hg. By diffusion, the dye traveled distally and stained the artery proximal to the occluder. A dilute solution of dye was also placed in the open end of the artery. This stained the artery distal to the occluder. With the occluder still applied, the segment of artery 1 mm distal and proximal on either side of the occluder was resected and washed in saline. The occluder was then removed and the artery was opened. The unstained area was measured under the microscope, and a segment 1.5 mm long and 0.4 mm wide, representing an area of 0.6 mm$^2$, was obtained. Using the measurements of arterial pressure and the occluding area, we calculated the clamp force exerted at the various application points.

Scanning electron microscope evaluation

Thirty Sprague-Dawley rats weighing between 350 and 500 g were divided randomly into a control group of 10 animals and an experimental group of 20 animals. The rats were anesthetized with pentobarbital (40 mg/kg intraperitoneally) followed by the subcutaneous administration of 0.4 mg of atropine. Both carotid arteries were dissected and prepared for application of the occluder using the operating microscope.

In the 10 control rats, the occluder was placed on the right and left carotid arteries, but occlusion was not performed. The right carotid arteries were recovered at 75 minutes and the left carotid arteries at 135 minutes. The arteries were excised under the operating microscope using $25\times$ magnification, opened longitudinally, and washed gently with Ringer's lactage solution. The flattened arteries were then fixed with 2% buffered glutaraldehyde and prepared for scanning electron microscopy. The endothelial surface of the specimens were examined at $40\times$ to $16,000\times$ using an AMR scanning electron microscope (Advanced Metal Research, Burlington, Mass.).

In the experimental group, the occluder was placed on the carotid arteries, and the cuff-to-base distance was adjusted to the point at which blanching of the vessel was observed between the blades of the occluder and arterial pulsations were dampened. The occluder was applied for 1 hour to the right carotid arteries and 2 hours to the left carotid arteries. Before recovery of the specimens, blood flow was restored for 15 minutes. The arteries were ligated both proximal and distal to the occluded area, excised, and prepared for scanning electron microscopy in the same manner as for the control group. The endothelial alterations were assessed by the classification of Dujovny et al.

RESULTS

Mechanical Evaluation

The occluder was effective in preventing flow through a wide range of pressures (80 to 375 mm Hg) that varied directly with the base-to-cuff distance (2 to 10 mm). The clamp force calculated was based on the occlusive area of 0.6 mm$^2$. These findings were compatible with our previous measurement for minimal occlusive force.

Results of Scanning Electron Microscopy

The 10 control specimens showed a uniform architecture of fine longitudinal ridges and folds about 15 pm wide. Their smooth undulations comprised a normal pattern.

The experimental specimens occluded for 1 hour with a temporary vascular occluder presented endothelial changes, in the "corner-mirror" configuration. Varying degrees of endothelial changes, ranging from relatively mild flattening to moderate flattening, were found in all experimental specimens. Endothelial ridge or fibrin, platelet, or red blood cell deposits were observed in any experimental specimens (FIG. 3). Specimens recovered after 1 hour showed milder endothelial changes than did those recovered 2 hours after application of the occluder. No thrombus formation was observed at the site of occlusion in any of the specimens (FIG. 4).

SUMMARY

With its rounded contour flexibility, the present occluder causes a minimal degree of endothelial damage, even after 2 hours of application, and the pliable tubing allows gentler contact with the vessel than that occurring with conventional rigid metallic clips. The transparency, the large force spectrum, and the ability to observe directly the blanching and cessation of blood flow are other factors of efficacy and safety. Also, the occluder is smaller than any conventional temporary clip, thus enlarging the operative field. Moreover, the fact that the occluder is perfectly smooth, with no sharp edges, precludes the hazard of suture entanglement.

We have found, using the scanning electron microscope, that the blood products that tend to adhere after the use of either the occluder or a microclip are difficult to remove even with ultrasonic cleaning. Ideally, therefore, only one application per clinical case is advisable. However, the economics of using the microclip on a disposable basis make it a very expensive surgical item.

The microvascular occluder has been used widely in experimental animal anastomoses ranging in vessel size from 0.75 to 2.8 mm in rat, rabbit, guinea pig and dog microvessels. The occluder has also been used clincally in the performance of a superficial temporal artery to middle cerebral artery bypass graft, where it was found to be entirely adequate in maintaining occlusion of the cortical artery.

Although the occluder is a relatively simple device, the principle of using a soft material and a system that allows adjustment of the occlusive force on an individual basis has made the microvascular occluder a versatile and reliable surgical tool. The ability to visualize the cessation of blood flow, the large force spectrum, and the lower potential for the development of vascular thrombosis open a new dimension in temporary vascular occlusion.

Referring to FIG. 9, a holder 38 comprises means for orienting a pair of occluders 10 in longitudinally spaced relation along the length of a vessel section. The holder 38 comprises a tubular sleeve 40, open at opposite ends and having a longitudinal slit, or slot 42, end-to-end, i.e., communicating with the open ends. The occluders 10 have the bases 12 thereof, inserted into the open ends of the holder 38, and the arms thereof project in spaced parallel relation from the holder. The clamping cuff of the occluders are tightened in the manner described above, and because of the relatively small size, the holder is a novel adjunct to the novel occluders per se.

The occluder and/or holder heretofore described, are of a material readily adapted for sterilization in an atmosphere of ethylene oxide using conventional, operating room sterilization procedures and techniques. Additionally, because the device is conducive to Mass-Manufacture from relatively inexpensive materials, it lends itself to ready use and adaption.

As various changes could be made without departing from the scope of the invention, it is intended that all matters contained in the above description or shown in the accompanying drawing shall be interpreted as illustrative and not in a limiting sense, the invention being defined in the appended claims.

What is claimed is:

1. A microvascular occluder comprising a base integral with a stem, said stem comprising a pair of compressible, non-inflatable, tubular arms projecting in proximate, normally-divergent relationship from said base for capturing a blood vessel immediately at said base and extending transversely between said arms, each of said arms comprising a normally-soft, tubular element, one of said arms being shorter than the other and having a free end; said arms having a rounded contour-flexibility and pliability for providing gentle contact with a blood vessel being compressed and causing minimal endothelia damage to said blood vessel when it is being compressed; and cuff means comprising a sleeve on said other arm and normally captured thereon and slidable over said free end of said one arm and over both said arms in unison for gradually and progressively compressing said arms onto the captured transverse blood vessel between said cuff means and said base for gradually and softly applying pressure to said transverse blood vessel with minimal degree of endothelial damage and occluding the passage of blood therethrough, said other arm having stop means thereon for capturing the cuff means thereon, said base comprising a flat element integral with adjacent ends of said arms and sealing them off thereat, said base extending laterally of said adjacent ends of said arms and maintaining said arms in the normal divergent relationship when said occluder is being applied on a said blood vessel and providing means for handling said occluder and providing means for supporting said occluder in an operative position.

2. The structure as claimed in claim 1 in which at least one of said arms includes indicia means comprising graduations spaced along the length thereof and with which said cuff means is alignable for determining the distance of said cuff means from said base when applying pressure during an occluding procedure.

3. The structure as claimed in claim 1 in which said shorter leg is terminally beveled at its free end away from said other leg whereby when the arms are juxtaposed the beveled portion merges into the adjacent surface of said other arm for facilitating sliding of said cuff means thereover.

4. The structure as claimed in claim 1 in which said arms are tubular sleeves having an inner diameter of 0.27 mm and an outer diameter of 0.6 mm, said cuff means comprising a tubular element having an outer diameter of 1.7 mm and an inner diameter of 1.2 mm, said cuff means being slidable over the two arms when the arms are in juxtaposition and fitting snugly in circumposed relation thereabout.

* * * * *